(12) United States Patent
Zeng et al.

(10) Patent No.: US 10,499,940 B2
(45) Date of Patent: Dec. 10, 2019

(54) APPARATUS FOR REMOVING CALCULUS IN VITRO

(71) Applicant: ZHENGZHOU FUJIANDA MEDICAL EQUIPMENT CO., LTD., Zhengzhou, Henan (CN)

(72) Inventors: Guohua Zeng, Guangzhou (CN); Fujian Cao, Zhengzhou (CN); Changbao Xu, Zhengzhou (CN); Zhiqiang Chen, Wuhan (CN)

(73) Assignee: Zhengzhou Fujianda Medical Equipment Co., Ltd., Zhengzhou (CN)

( * ) Notice: Subject to any disclaimer, the term of this patent is extended or adjusted under 35 U.S.C. 154(b) by 822 days.

(21) Appl. No.: 14/778,951

(22) PCT Filed: Mar. 22, 2013

(86) PCT No.: PCT/CN2013/073075
§ 371 (c)(1),
(2) Date: Jan. 15, 2016

(87) PCT Pub. No.: WO2014/146299
PCT Pub. Date: Sep. 25, 2014

(65) Prior Publication Data
US 2016/0120559 A1    May 5, 2016

(51) Int. Cl.
*A61B 17/225*    (2006.01)
(52) U.S. Cl.
CPC ...... *A61B 17/2255* (2013.01); *A61B 17/2256* (2013.01)

(58) Field of Classification Search
CPC .................. A61B 17/2251; G10K 15/06
See application file for complete search history.

(56) References Cited

U.S. PATENT DOCUMENTS

| | | | | |
|---|---|---|---|---|
| 4,326,506 A | * | 4/1982 | Kawabata | A61H 1/00 5/694 |
| 4,984,575 A | * | 1/1991 | Uchiyama | A61B 17/2255 600/439 |
| 5,542,907 A | * | 8/1996 | Chou | A61H 23/0263 601/46 |

(Continued)

FOREIGN PATENT DOCUMENTS

CN    1650810    * 10/2005

*Primary Examiner* — Hien N Nguyen
(74) *Attorney, Agent, or Firm* — Lewis Roca Rothgerber Christie LLP

(57) ABSTRACT

Disclosed is a lithagogue equipment in vitro, comprising a vibrating bed (10) and a control device (20) located externally, wherein said vibrating bed (10) includes a primary oscillator (111) located above a bed body (102) and connected therewith via an adjustable mechanical arm (108) and a sub oscillator (107) protruding from an upper surface of the bed body (120), wherein said control device (20) is used for controlling the vibration of the primary oscillator (111) and the sub oscillator (107) and the movement of the bed body (102). Said control device (20) and said vibrating bed (10) are separated from each other, and a display (201) is arranged on the control device (20). Accordingly, medical personnel are able to timely adjust the vibrating bed (10), the primary oscillator (111) and the sub vibrator (107) based on the calculus condition displayed via the display (201), greatly improving the operational efficiency.

16 Claims, 3 Drawing Sheets

(56) References Cited

U.S. PATENT DOCUMENTS

| | | | |
|---|---|---|---|
| 2005/0015027 A1* | 1/2005 | Kojima | A61H 23/0236 601/57 |
| 2005/0132494 A1* | 6/2005 | Koga | A61G 7/0005 5/605 |
| 2007/0038159 A1* | 2/2007 | Buchholtz | A61B 17/22004 601/4 |
| 2012/0271166 A1* | 10/2012 | Shao | A61B 5/4869 600/438 |
| 2012/0311783 A1* | 12/2012 | Chiang | A47C 21/08 5/421 |

* cited by examiner

APPARATUS FOR REMOVING CALCULUS IN VITRO

CROSS-REFERENCED TO RELATED APPLICATION(S)

This Application is a National Phase Patent Application of, and claims priority to and the benefit of International Application Number PCT/CN2013/073075, filed on Mar. 22, 2013, the entire content of which is incorporated herein by reference.

FIELD OF THE INVENTION

The present invention relates to the technical field of medical device, and more particularly, to a lithagogue equipment in vitro.

BACKGROUND OF THE INVENTION

Urinary calculus is a common disease, which has been threatened to human health. Recently, with the further study of the causes of urinary calculus, the common treatment methods thereof mainly includes: 1) take lithagogue medicine, of which the effect is not good enough and brings side effect; 2) extracorporeal shock wave lithotripsy (ESWL) technique, which is difficult to operate and required repeated treatments, and it is easily to have lithotripsy residual after the treatment which is harmed to the kidney; 3) the treatment of percutaneous nephrolithotomy (PCNL), Ureteroscopic lithotripsy (URL), and laparoscopic ureterolithotomy (LS) and the like, which have disadvantages such as having expensive costs, high risk, more complication and the residual calculus being hardly removed.

In order to solve above problems, a multi-functional renal calculus lithagogue machine was disclosed in a Chinese Patent Application (Application No. CN 93112128), which is composed of a bouncing device, a percussion device, an electrotherapy device, an electrical control device, a supporting cabinet, a platform and so on. Such machine combines percussive, bouncing and electrotherapeutic functions which are functionally and cooperated together so as to perform lithagogue treatment for various parts of the human body separately or synchronously. However, such machine is unable to immediately detect the lithagogue result, thus it is difficult to ensure the lithagogue effect.

In another Chinese Application, of which the application number is 200410004386.X, a urinary working stage was disclosed. The urinary working stage includes a U-shaped arched frame, an X-ray resource is provided at one end of the frame, and an image processing device is provided at the other end of the frame. The image processing device is cooperated with the X-ray resource. The urinary working stage further includes an examination platform connected to the U-shaped arched frame. The X-ray resource and the image processing device can be moved independently in relative to the U-shaped arched frame. A comminuting treatment head, by which performs the lithagogue treatment of the human urinary, is provided on the U-shaped arched frame. However, during the treatment, the working stage cannot synchronously adjust the position of the treatment platform based on the examined result so as to be unable to obtain a better effect.

Therefore, there is a need to have a lithagogue equipment in vitro which is easily to be operated and obtain a good lithagogue effect.

SUMMARY OF THE INVENTION

It is an object of the present invention to provide a lithagogue equipment in vitro, to overcome the shortage of being difficult to operate of the existing lithagogue equipment in vitro.

One aspect of the present invention is to provide a lithagogue equipment in vitro, characteristics in that, said lithagogue equipment comprises a vibrating bed and a control device provided outside the vibrating bed; said vibrating bed includes a primary oscillator located above a bed body and connected with said bed body via an adjustable mechanical arm, and a sub oscillator protruding from an upper surface of said bed body, said control device is used to control the vibration of the primary oscillator and the sub oscillator and the movement of the bed body.

Preferably, a distance between said control device and the bed body is in a range of 1-20 meters.

Preferably, a scanning imaging device is provided above said bed body and adjustably combined with said bed body, said control device includes a displaying device and a work station, said work station transfers images scanned by the scanning imaging device to said displaying device.

Preferably, said bed body further comprises a base, and a rotating shaft provided between said base and said bed body, wherein the bed body is rotatable in a horizontal direction and a vertical direction by a range of −45° to +45° around the rotating shaft in respect to the base and taking said rotating shaft as a center.

Preferably, an operating handle is provided at the upper surface of the control device for controlling the movement of the bed body.

Preferably, said control device includes a plurality of control buttons for controlling the vibration of said primary oscillator, the vibration of said sub oscillator, movements of said adjustable mechanical arm and said scanning imaging device, and the vibrating strength of said primary oscillator and said sub oscillator.

Preferably, said bed body is provided with a pillow at one end thereof and a foot baffle at another end thereof, said sub oscillator is protruded from the upper surface of the bed body between said pillow and said foot baffle.

Preferably, said sub oscillator is shaped in square with four corners in arc-shaped, a length of the said of the sub oscillator is in a range of 200-300 mm, and a height of the sub oscillator apart from the upper surface of the bed body is adjustable in a range of 20-50 mm.

Preferably, said sub oscillator is vibrated linearly or in wave shape, the amplitude of the sub oscillator is in a range of 1-10 mm, and the frequency thereof is in a range of 0-50 HZ.

Preferably, said adjustable mechanical arms includes a plurality of branch arms, any two of adjacent mechanical arms are connected therebetween by a joint, and said adjustable mechanical arm is able to rotate in a horizontal direction and adjust the height thereof.

Preferably, said main oscillator has a cylindrical shape with a diameter in a range of 40-60 mm and a height in a range of 150-180 mm, and a globate vibrating head is provided at a distal end of the primary oscillator and the diameter of the globate vibrating head is in a range of 45-55 mm.

Preferably, the amplitude of the primary oscillator is in a range of 1-10 mm and the frequency thereof is in a range of 0-50 HZ; the vibrating mode of the primary oscillator is as following: the frequency thereof is gradually increased from 0 to 50 Hz, and after being kept at 50 Hz for 5-10 minutes, the frequency is reduced from 50 Hz to 0.

Preferably, a pressure sensor is provided inside of the primary oscillator, the pressure value applied by the primary oscillator is displayed by the displaying device of the control device.

Preferably, a safety belt is provided at the upper surface of the bed body.

Preferably, said work station is used for storing the images transferred by the scanning imaging device and retrieving the images as needed.

The primary oscillator and the sub oscillator are added in the present invention on the basis of the existing lithagogue equipment in vitro. The lithagogue effect is improved by combining the vibration of the primary oscillator and the sub oscillator.

The control device and the vibration bed are separated from each in the present invention, and the displaying device is provided on the control device. Thus, the doctor can timely adjust the vibration bed, the primary oscillator and the sub oscillator according to the calculus condition displayed in the displaying device so as to extremely improve the operation efficiency.

The bed body in the present invention can be moved in the horizontal and vertical directions at a wide angle. Since according to the physiological excreting pathway of the human organs, the lithagogue path of different organs and different part requires different lithagogue position, thus, the direction of the bed body can be changed according to the calculus condition of the patient.

The working position of the primary oscillator of the present invention can be adjusted in several orientations, so that the calculus in each location inside the urinary system can be effectively removed by adjusting the working position of the primary oscillator.

The length and the width of the sub oscillator are near to the size of the urinary system. The height of the sub oscillator also can be adjusted according to the degree of obesity and the depth of the back dimple of the human body, and both the amplitude and the frequency thereof are adjustable. Each renal of a normal adult has a length in a range of 100-120 mm, the length and the width of the sub oscillator in the present invention is in a range of 200-300 mm, which is just close to the area of the urinary system of the normal adult. Furthermore, the height of the sub oscillator in respect to the vibrating bed also can be adjusted in the range of 20-50 mm, so that according to the age and the degree of obesity of different patients, the sub oscillator always can be attached to the treatment area at back of the patient after adjusting. Therefore, the present invention greatly improves the effect of the calculus treatment by changing under different operating conditions with the humanization design of the sub oscillator.

The vibrating frequency of the sub oscillator of the present invention is increased from 0 to 50 HZ, and after kept at 50 HZ for a while, reduced from 50 HZ to 0. By gradually increasing and reducing the frequency, the equipment in the present invention is more humanized so as to allow the patient to be able to adapt the treatment process slowly; the purpose of the frequency holding for a certain times at 50 HZ is: for the calculus having different size, only holding the frequency at 50 HZ for a certain time can allow the calculus to throw and move in the urinary system channel and then excreted along the physiological excretion channel.

The scanning imaging device is able to only scan the urinary system, but also display the image in the displaying device, thus, the operating doctor is able to adjust the working position and the vibrating strength of the primary oscillator according to the particular situation and determine whether the movement of the body bed is required to be controlled and the treatment is required to be stopped.

DETAILED DESCRIPTION OF THE EMBODIMENTS

Figure 1:
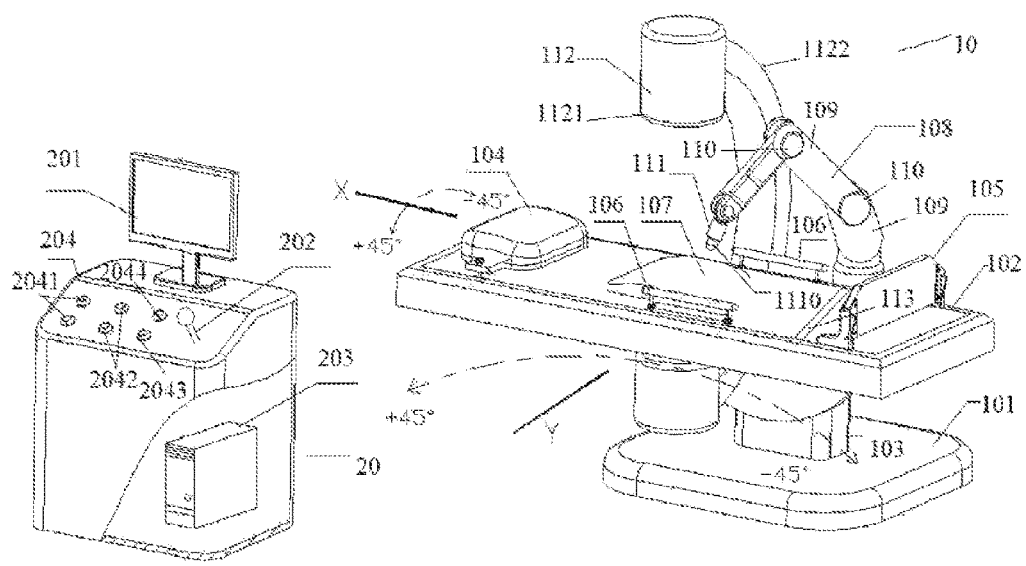
FIG. 1 shows a lithagogue equipment in vitro according of the present invention.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

Embodiment I

As shown in FIG. 1, a lithagogue equipment in vitro includes a vibrating bed 10 and a control device 20 for controlling the movement of the vibrating bed. The vibrating bed 10 and the control device 20 are separated from each other by 2 meters.

The vibrating bed comprises a base 101 and a bed body 102 located above the base 101, the bed body 102 is connected to the base 101 through a rotating shaft 103 which is vertical to the horizontal plane. The bed body 102 is rotatable in respect to the base 101 in a horizontal direction and a vertical direction, that is, in a range of −45° to +45° in an X-axis and a Y-axis directions.

Furthermore, the bed body 102 should be installed in an X-ray protection room, and an operation platform is installed outside the X-ray protection room, so that the operating doctor can be protected from the harm caused by X-ray.

A pillow 104 is provided at one end of an upper surface of the bed body 102, and a foot baffle 105 is provided at the other end. Arms 106 are respectively arranged at the left and the right sides of the bed body 102. A sub oscillator 107 protruding from the upper surface of the bed body 102 is arranged at the right middle between the pillow 104 and the foot baffle 105. The surface area of the sub oscillator 107 is 240 mm*240 mm, so that the sub oscillator just faces to the waist of the human body lying on the vibrating bed 10. A height of the sub oscillator protruding from the upper surface of the vibrating bed can be adjusted in a range of 20-50 mm, so that for patients having different ages and obesity degree, the sub oscillator always just attaches to the flank of the human body.

A motor having an eccentric rotating shaft is arranged inside the sub oscillator 107, so that the eccentric motor is able to produce high frequency vibration, that is, the amplitude is between 1-10 mm and the vibrating frequency is between 0-50 HZ. Also, the sub oscillator 107 is able to not only vibrate linearly, but also vibrate in wave shape in relative to the bed body. The form of the vibration depends on the condition of the calculus of a patient.

A mechanical arm 108 is jointed to one side of the upper surface of the bed body 102. The mechanical arm 108 is an adjustable structure, which includes a plurality of branch arms connected therebetween with joints 110. Through the movement of the joints 110, the position of the whole mechanical 108 is able to be adjusted up and down and left and right.

The branch arm 109 at a distal end of the mechanical arm 108 has one end coupling to the primary oscillator 111, the primary oscillator 111 has a cylindrical shape with a diameter in 50 mm and a height in 160 mm. A globate vibrating head 1110 is provided at the distal end of the primary oscillator 111, and the diameter of the globate vibrating head 1110 is 50 mm. The globate vibrating head 1110 is able to vibrate at the desired position at the human body. Both the primary oscillator 111 and the sub oscillator 107 are mechanical oscillators. The globate vibrating head 1110 of the primary oscillator 111 is able to move linearly in up and down directions, and the amplitude thereof is in a range of 1-10 mm and the frequency thereof is in a range of 0-50 HZ. The vibrating mode of the primary oscillator is as following: the frequency thereof is gradually increased from 0 to 50 Hz, and after being kept at 50 Hz for a certain time, the frequency is reduced from 50 Hz to 0. At any frequency between 0 to 50 Hz, the primary oscillator is able to vibrate with a fixed frequency for several seconds and stop for several seconds, and repeatedly vibrate as the above. Furthermore, a pressure sensor is disposed inside the primary oscillator. The primary oscillator may apply different pressure based on different ages, weight and diseases of patients during the treatment. The pressure value applied by the primary oscillator can be displayed on a displaying device of the control device.

An X-ray scanning imaging device 112 with a digital electronic computer is provided at the same side where the mechanical arm 108 is provided on the upper surface of the bed body 102. The scanning imaging device 112 includes a scanning head 1121 and a connecting rod 1122. The scanning rod 1121 just faces to the sub oscillator 102 and exactly is used for scanning the urinary system of the human body above the sub oscillator 107.

A safety belt 113 for preventing the patient from falling down the bed during the treatment is further provided on the upper surface of the bed body 102.

The control device 20 includes a displaying device 201 incorporated on an upper surface of the control device and an operating handle 202 is disposed nearby the upper surface. The handle 202 is moved in four directions which are upward, downward, leftward and rightward. By the movement of the handle 202, the vibrating bed also can move in the horizontal direction and the vertical direction, i.e. in X-axis direction and Y-axis direction shown in the figure. A plurality of control buttons 204 are arranged nearby the handle 202, wherein the mechanical arm control button 2043 is used to control the movement of the mechanical arm 108 of the primary oscillator in respect with the bed body 102. A primary oscillator control button 2041 is used to control the vibration of the primary oscillator and adjust the strength of the vibration. A sub oscillator control button 2042 is used to control the vibration of the sub oscillator 107 and adjust the strength of the vibration. A control button 2044 of the scanning imaging device 112 is used to control the movement of the scanning imaging device 112.

The control device 20 further includes a working station 203 in the internal of the control device 20. The displaying device 201 is connected with the scanning imaging device 112 through the working station 203.

The working station 203 is used to receive the image data delivering from the scanning imaging device 112 and display images on the displaying device 201 after converting such image data. Furthermore, the working station 203 may store scanning images at respective selected time so as to be convenient for doctors filing and searching.

Figure 2:
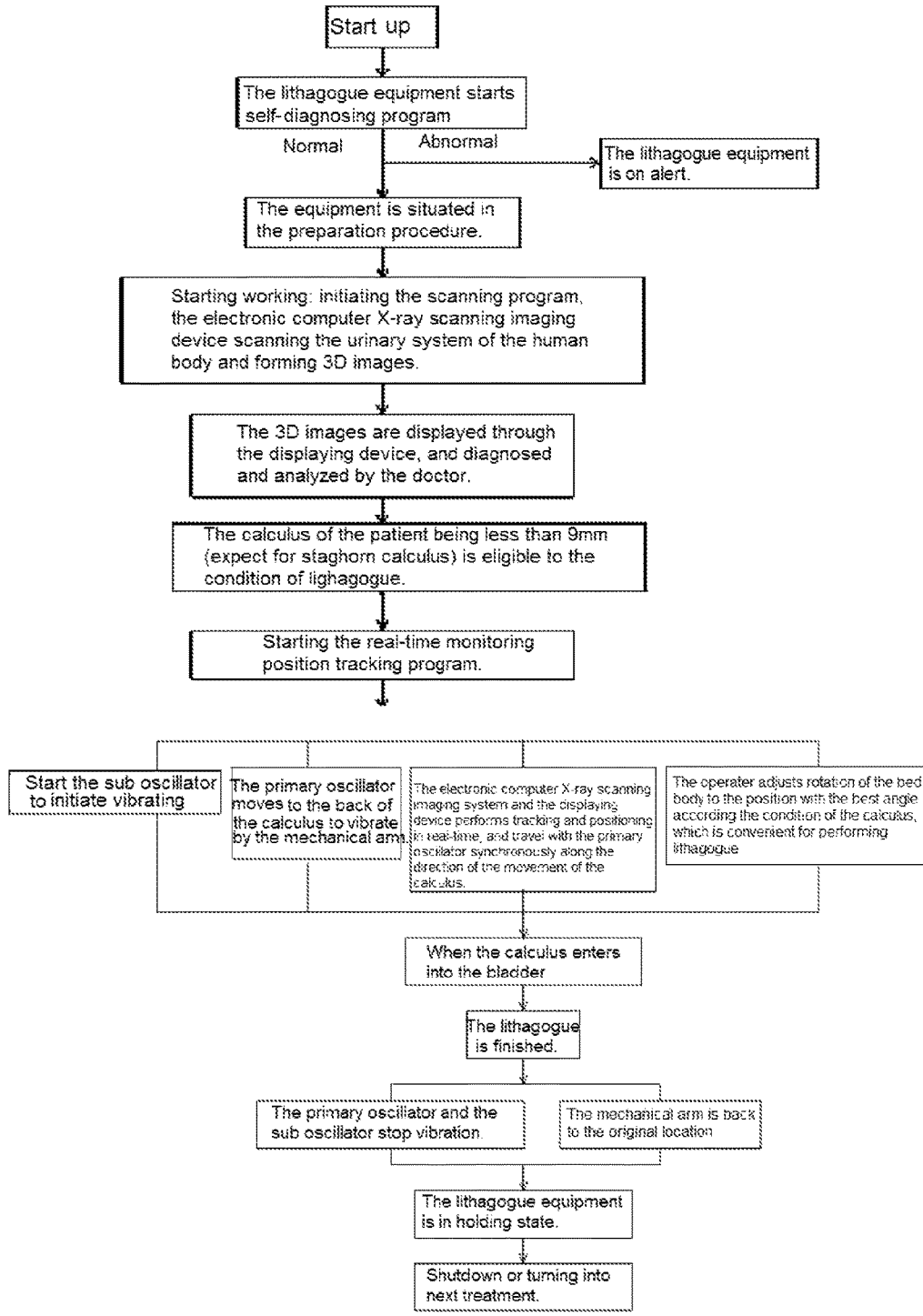
FIG. 2 shows a working process of the lithagogue equipment in vitro according to the present invention.

Refer to FIG. 2, during the operation, firstly, the patient lies on the bed body 102, and the doctor starts the control device 20. The lithagogue equipment starts self-diagnosing procedure. If it shows that the self-diagnosing result is normal, the lithagogue equipment enters into a preparation step; if it shows that self-diagnosing result is abnormal, then the lithagogue equipment is on alert.

Then the whole lithagogue equipment is started to work, the working station 203 is initiated the scanning procedure, the X-ray scanning imaging device 112 scans the urinary system of the human body and form 3D images. The scanned image is displayed through the displaying device 201, and the operating doctor may diagnose and analyze the shape and the size of the calculi and whether the urinary path being unblocked and having lesions and malformation based on the condition of the urinary calculus observed from the displaying device 201.

When the calculi of the patient is less than 9 mm, expect for staghorn calculus, if the calculus condition is eligible to the condition of lithagogue, the operating doctor may start a real-time monitoring position tracking procedure.

The operating doctor first manipulates the control handle of the control device based on the calculus condition of the patient, pulls the control handle leftward so as to trigger a switch provided at the left side of the control handle, so that the motor starts to rotate forwardly in a Y-axis direction of the bed body, i.e. in the vertical direction mentioned above, and the motor drives the bed body to start to rotate +45° in the Y-axis direction. When the bed body rotates +45°, the bed body triggers the travel switch, so that the motor is stopped and the bed body is stopped to rotate.

When the operating doctor pulls the control handle rightward so as to trigger a switch provided at the right side of the control handle, the motor starts to rotate backwardly in the Y-axis direction of the bed body, i.e. in the vertical direction mentioned above, and the motor drives the bed body to start to rotate −45° in the Y-axis direction. When the bed body rotates −45°, the bed body triggers the travel switch, so that the motor is stopped and the bed body is stopped to rotate.

When the operating doctor pulls the control handle upwardly so as to trigger a switch provided at the upper side of the control handle, the motor starts to rotate forwardly in a X-axis direction of the bed body, i.e. in the horizontal direction mentioned above, and the motor drives the bed body to start to rotate −45° in the X-axis direction. When the bed body rotates −45°, the bed body triggers the travel switch, so that the motor is stopped and the bed body is stopped to rotate.

When the operating doctor pulls the control handle downwardly so as to trigger a switch provided at the lower side of the control handle, the motor starts to rotate backwardly in the X-axis direction of the bed body, i.e. in the horizontal direction mentioned above, and the motor drives the bed body to start to rotate +45° in the X-axis direction. When the bed body rotates +45°, the bed body triggers the travel switch, so that the motor is stopped and the bed body is stopped to rotate.

According to the physiological excreting pathway of the human organs, the calculus excreted from different organs and different part of the human body is required to have different excretion position. Therefore, the operating doctor needs to adjust the position of the bed body all the time to obtain the best lithagogue position.

When having right renal calculus, the patient should take a left prone position in which the bed body rotates to −45° along the X-axis; here, the renal hilum is downward, and the funnel and the renal hilum are vertical to each other in the up and down direction that is facilitate the calculus entering into the funnel and the ureter, and then performing lithagogue treatment according to the ureteral calculus position.

When having left renal calculus, the patient should take a right prone position in which the bed body is rotated to +45° along the X-axis; here, the renal hilum is downward, and the funnel and the renal hilum are vertical to each other in the up and down direction that is facilitate the calculus entering into the funnel and the ureter, and then performing lithagogue treatment according to the ureteral calculus position.

When having calculus in upper pole of renal, the patient should take a dorsal elevated position in which the bed body is rotated to −45° along the Y-axis; here, the renal hilum is downward, and the funnel and the upper pole of renal are vertical to each other in the up and down direction that is facilitate the calculus entering into the funnel and the ureter, and then performing lithagogue treatment according to the ureteral calculus position.

When having calculus in lower pole of renal, the patient should take a trendelenburg position in which the bed body is rotated to +45° along the Y-axis; here, the level of the lower pole of renal is higher than the upper pole of renal so as to facilitate the calculus entering into the renal pelvis funnel portion from the inside of the renal calices of the lower pole of renal; and then, the patient is turned into dorsal elevated position that the bed body is rotated to −45° along the Y-axis, here, the level of the upper pole of renal is higher than the lower pole of renal, so as to, after the calculus inside the renal pelvis is entered into the ureter, perform lithagogue treatment according to the ureteral calculus position.

In order to prevent the patient falling from the bed during the movement of the bed body, the patient is fixed on the upper surface of the bed body by the safety belt 113.

Furthermore, the operating doctor may adjust the movement of the mechanical arms 108 by adjusting the mechanical arm control button 2043 so as to move the vibrating head 1110 of the primary oscillator 111 to vibrate at the back of the calculus.

At the same time, the operating doctor may turn on the sub oscillator control button 2042 of the sub oscillator 107 to allow the sub oscillator 107 to vibrate. Further, the vibrating strength of the primary oscillator 111 can be controlled by adjusting the control button 2041 of the primary oscillator 111, and the vibrating strength of the sub oscillator 107 can be controlled by adjusting the control button 2042 of the sub oscillator 107.

The sub oscillator 107 produces high frequency vibration, and at the same time, the primary oscillator 111 also produces high frequency vibration in the calculus focal area, and such high frequency vibration is transferred to the calculus action area via the human tissues, which allows the calculus to free and move out of the original location.

The operating doctor further operates the control button 2044 of the scanning imaging device to control the scanning imaging device 112 to move synchronously with the primary oscillator in the moving direction of the calculus, and to perform scanning, tracking and positioning in real-time. Also, according to the calculus condition continually changing in vivo, the working position and vibrating strength of the primary oscillator 111 and sub oscillator 107 are adjusted. And the operating doctor determines whether the treatment is finished based on the changed calculus condition.

The primary oscillator 111 is activated at the back of the free calculus to vibrate linearly and to push the calculus to move forward. The operating doctor moves the bed body 102 with a best slop facilitating calculus removing according to the structural features of the human organs by adjusting the movement of the operating handle 202, and then the calculus is entered into the bladder along the urinary by adjusting the movements of the main oscillator 111 and the sub oscillator 107. When the lithagogue is finished, the main oscillator 111 and the sub oscillator 107 are turned off, and the mechanical arms 108 of the main oscillator are returned to the original position. The lithagogue equipment is shutdown, or in holding state, or entered into next round of the treatment.

Embodiment II

Figure 3:
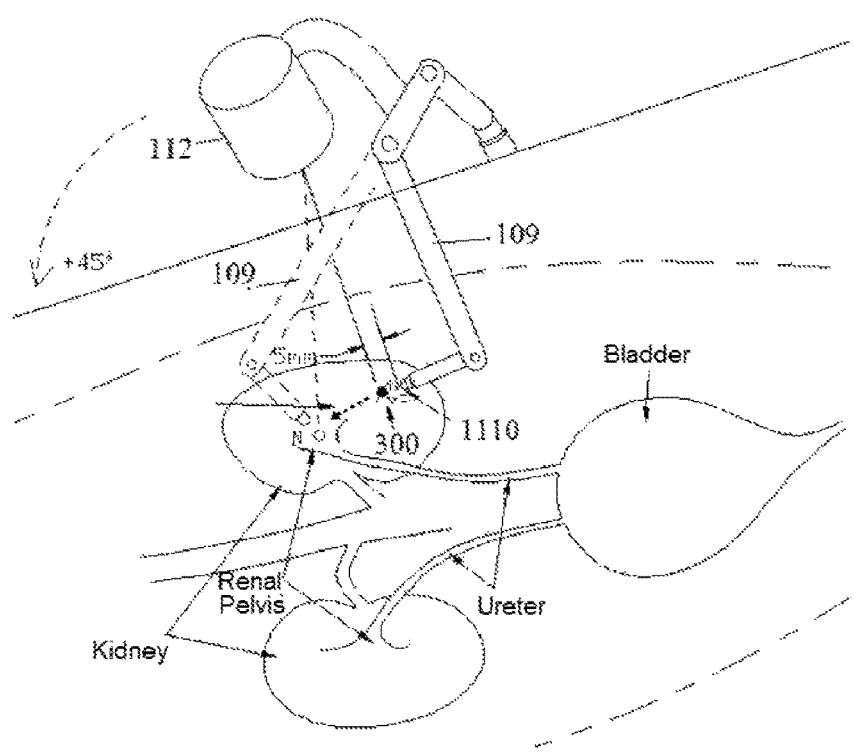
FIG. 3 shows a first movement status of the calculus in a body moved by a primary oscillator.

FIG. 3 shows a first state diagram of the calculus in the urinary system under the action of the primary oscillator. At this time, the comminuted calculus 300 in the renal is gradually moved toward the inlet of the ureter.

Figure 4:
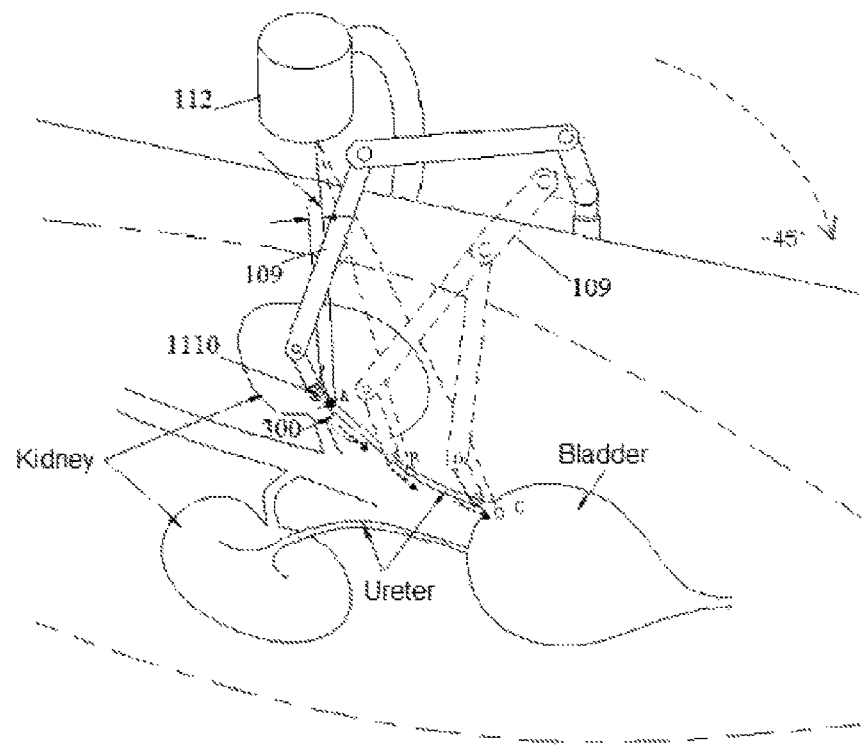
FIG. 4 shows a second movement status of the calculus in the body moved by the primary oscillator.

FIG. 4 shows a second state diagram of the calculus in the urinary system under the action of the primary oscillator. By comparing FIG. 3 and FIG. 4, the comminuted calculus is kept moving in the ureter until moved to the bladder under the action of the vibrating head 1110 of the main oscillator.

It would be appreciated by those skilled in the art that many modifications, alterations and substitutions may be made in these embodiments without departing from the principles and spirit of the invention, the scope of which is defined in the claims and their equivalents.

What is claimed is:

1. A lithagogue equipment in vitro, characteristics in that, said lithagogue equipment comprises a vibrating bed and a control device provided outside the vibrating bed; said vibrating bed includes a primary oscillator located above a bed body and connected with said bed body via an adjustable mechanical arm, and a sub oscillator protruding from an upper surface of said bed body, said control device is used to control the vibration of the primary oscillator and the sub oscillator and the movement of the bed body, wherein a length of the sub oscillator is in a range of 200-300 mm, and a height of the sub oscillator from an upper surface of the bed body is adjustable in a range of 20-50 mm such that the sub oscillator is configured to be attached to a treatment area in a waist region of a patient, wherein the primary oscillator and the sub oscillator are configured to remove a renal calculus with a vibrating frequency of 50 Hz or less, wherein said lithagogue equipment further comprises a scanning imaging device which is provided above said bed body and adjustably combined with the bed body, said control device includes a displaying device and a work station, the work station transfers images scanned by the scanning imaging device to the displaying device, and wherein a pressure sensor is provided inside of the primary oscillator, the pressure value applied by the primary oscillator is displayed by the displaying device of the control device.

2. The lithagogue equipment in vitro according to claim 1, characteristics in that, a distance between said control device and the bed body is in a range of 1-20 meters.

3. The lithagogue equipment in vitro according to claim 1, characteristics in that, said bed body further comprises a base, and a rotating shaft provided between said base and said bed body, wherein the bed body is rotatable in a horizontal direction and a vertical direction by a range of −45° to +45° around the rotating shaft in respect to the base and taking said rotating shaft as a center.

4. The lithagogue equipment in vitro according to claim 1, characteristics in that, an operating handle is provided at the upper surface of the control device for controlling the movement of the bed body.

5. The lithagogue equipment in vitro according to claim 2, characteristics in that, said control device includes a plurality of control buttons for controlling the vibration of said primary oscillator, the vibration of said sub oscillator, the movements of the adjustable arm and the scanning imaging device, and the vibrating strength of said primary oscillator and said sub oscillator.

6. The lithagogue equipment in vitro according to claim 1, characteristics in that, said bed body is provided with a pillow at one end thereof and a foot baffle at another end thereof, said sub oscillator is protruded from the upper surface of the bed body between said pillow and said foot baffle.

7. The lithagogue equipment in vitro according to claim 6, characteristics in that, said sub oscillator is shaped in square with four corners in arc-shaped.

8. The lithagogue equipment in vitro according to claim 1, characteristics in that, said sub oscillator is vibrated linearly or in wave shape, the amplitude of the sub oscillator is in a range of 1-10 mm, and the frequency thereof is in a range of 0-50 Hz.

9. The lithagogue equipment in vitro according to claim 1, characteristics in that, said adjustable mechanical arm includes a plurality of branch arms, any two of adjacent branch arms are connected therebetween by a joint, and said adjustable mechanical arm is able to rotate in a horizontal direction and adjust the height thereof.

10. The lithagogue equipment in vitro according to claim 1, characteristics in that, said primary oscillator has a cylindrical shape with a diameter in a range of 40-60 mm and a height in a range of 150-180 mm, and a globate vibrating head is provided at a distal end of the primary oscillator and the diameter of the globate vibrating head is in a range of 45-55 mm.

11. The lithagogue equipment in vitro according to claim 1, characteristics in that, the amplitude of the primary oscillator is in a range of 1-10 mm and the frequency thereof is in a range of 0-50 Hz; the vibrating mode of the primary oscillator is as following: the frequency thereof is gradually increased from 0 to 50 Hz, and after being kept at 50 Hz for 5-10 minutes, the frequency is reduced from 50 Hz to 0.

12. The lithagogue equipment in vitro according to claim 1, characteristics in that, a safety belt is provided at the upper surface of the bed body.

13. The lithagogue equipment in vitro according to claim 1, characteristics in that, said work station is used for storing the images transferred by the scanning imaging device and retrieving the images as needed.

14. The lithagogue equipment in vitro according to claim 3, characteristics in that, an operating handle is provided at the upper surface of the control device for controlling the movement of the bed body.

15. The lithagogue equipment in vitro according to claim 7, characteristics in that, said sub oscillator is vibrated linearly or in wave shape, the amplitude of the sub oscillator is in a range of 1-10 mm, and the frequency thereof is in a range of 0-50 Hz.

16. The lithagogue equipment in vitro according to claim 10, characteristics in that, the amplitude of the primary oscillator is in a range of 1-10 mm and the frequency thereof is in a range of 0-50 Hz; the vibrating mode of the primary oscillator is as following: the frequency thereof is gradually increased from 0 to 50 Hz, and after being kept at 50 Hz for 5-10 minutes, the frequency is reduced from 50 Hz to 0.

* * * * *